United States Patent [19]

Igusa et al.

[11] Patent Number: 5,449,502
[45] Date of Patent: Sep. 12, 1995

[54] STERILIZING APPARATUS UTILIZING ULTRASONIC VIBRATION

[75] Inventors: Masaru Igusa, Takasaki; Hironobu Kurosawa, Isesaki, both of Japan

[73] Assignee: Sanden Corp., Isesaki, Japan

[21] Appl. No.: 319,617

[22] Filed: Oct. 7, 1994

Related U.S. Application Data

[63] Continuation-in-part of Ser. No. 998,435, Dec. 30, 1992, abandoned.

[51] Int. Cl.$^6$ ............................................. A61L 2/18
[52] U.S. Cl. ................................. 422/292; 239/102.2; 134/198
[58] Field of Search ................. 422/28, 20, 292; 239/102.2; 134/198

[56] References Cited

U.S. PATENT DOCUMENTS

| | | | |
|---|---|---|---|
| 4,296,068 | 10/1981 | Hoshino | 422/20 |
| 4,670,010 | 6/1987 | Dragone | 422/292 |
| 4,691,724 | 9/1987 | Garcia et al. | 134/184 |
| 4,726,524 | 2/1988 | Ishikawa et al. | 239/102.2 |
| 4,726,525 | 2/1988 | Yonekawa et al. | 239/102.2 |
| 4,799,622 | 1/1989 | Ishikawa et al. | 239/102.2 |
| 4,834,124 | 5/1989 | Honda | 134/184 |
| 4,844,343 | 7/1989 | Kurokawa et al. | 239/102.2 |
| 4,850,534 | 7/1989 | Takahashi et al. | 239/102.2 |
| 4,865,061 | 9/1989 | Fowler et al. | 134/184 |
| 4,888,516 | 12/1989 | Daeges et al. | 239/102.2 |
| 4,961,885 | 10/1990 | Aurahami et al. | 239/102.2 |
| 5,074,322 | 12/1991 | Jow | 422/292 |
| 5,095,925 | 3/1992 | Elledge et al. | 422/292 |
| 5,186,192 | 2/1993 | Netsu et al. | 134/184 |

FOREIGN PATENT DOCUMENTS 2089213 6/1982 United Kingdom .

*Primary Examiner*—James C. Housel
*Assistant Examiner*—Rachel Freed
*Attorney, Agent, or Firm*—Kenjiro Hidaka

[57] ABSTRACT

A sterilizing apparatus has a vertical ultrasonic horn with an output tip at the low end thereof and an antiseptic solution holding receptacle that is disposed in a manner that a part of the horn is inside the holding receptacle and the output tip is below a bottom wall of the holding receptacle. An antiseptic solution is first supplied into the holding receptacle that temporarily holds the solution. The solution gradually and continuously flows out from the holding receptacle through outlet holes, which are located in the bottom wall of the holding receptacle and contiguous with the horn, onto the surface of the output tip of the horn so that the horn, while vibrating at the ultrasonic frequency, causes the antiseptic solution to be atomized on the output tip and changed into a state of mist with which the sterilization is performed.

6 Claims, 7 Drawing Sheets

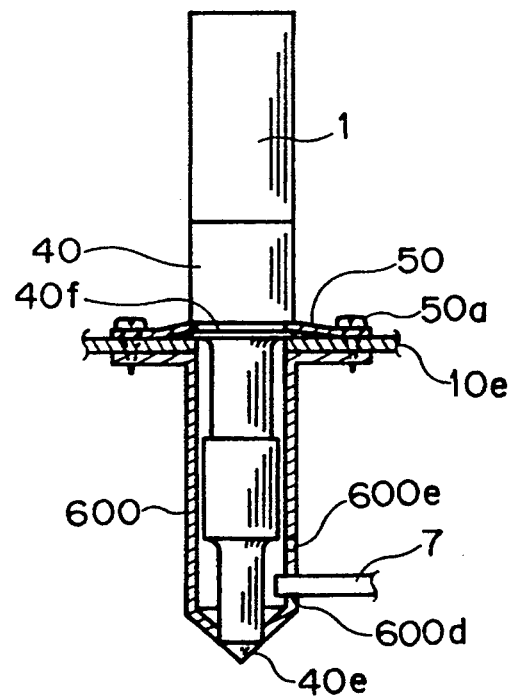
FIG.12
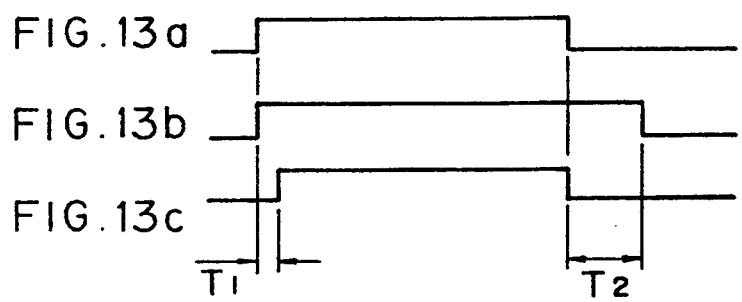

STERILIZING APPARATUS UTILIZING ULTRASONIC VIBRATION

This application is a continuation-in-part of application Ser. No. 07/998,435 filed Dec. 30, 1992.

BACKGROUND OF THE INVENTION

1. Field of the Invention

This invention pertains to a sterilizing apparatus utilizing an ultrasonic vibration for sterilizing fingers, hands, medical tools, tableware, food, etc., and particularly a sterilizing apparatus having a vibrator member which causes an antiseptic solution to be atomized by ultrasonic vibration.

2. Description of the Prior Art

A conventional sterilizing apparatus has a sterilizing room in a housing which is open to the front of the housing. Above the sterilizing room is disposed a nozzle from which a pressurized antiseptic solution is jetted downward so that the user extends his/her hands to the sterilizing room through the front opening to have his hands or fingers sprayed with the antiseptic solution.

One such conventional sterilizing apparatus is disclosed in Japanese published utility patent application, No. 60-7089, published Mar. 8, 1985.

However, such a conventional sterilizing apparatus involves an undesirable jetting sound as the antiseptic solution exits from the nozzle. Furthermore, since the spray angle is even about the vertical center axis of the nozzle, the antiseptic solution is sprayed downwardly in a conical form. A conically formed spray zone is not proper because the hands are normally placed side by side by the user under the nozzle, thereby occupying a laterally extended zone. Thus, the hands or fingers tend to be sterilized unevenly. In addition, the maximum spray angle by a conventional jet-type sterilizer is only about 70°. Therefore, the nozzle has to be installed upwardly sufficiently apart from the object to be sterilized, thereby causing the overall size of the apparatus to be increased. The jetted solution tends to splash out of the sterilizing room and it may reach the clothes or other parts of the user. A substantial quantity of the antiseptic solution is thus wasted. Further, the mechanism of a conventional sterilizing apparatus employing a nozzle is complex because the pressurized antiseptic solution has to be depressurized by a depressurizing device or a solution recovery device after the use of the apparatus in order to avoid dripping of the solution from the nozzle. Another problem pertaining to a nozzle-employed jet-type sterilizer is that any additive or impurities contained in the solution tend to cause the nozzle to be clogged, because the diameter of the nozzle is normally only 0.2 to 0.3 mm. Therefore, the nozzle has to be frequently cleaned. For example, a small quantity of glycerin is normally added to an ordinary antiseptic solution, such as a mixture of ethanol and distilled water, in order to prevent human skin from roughening, but the glycerin often causes the nozzle to be clogged.

SUMMARY OF THE INVENTION

In view of the above mentioned situation, the primary object of the present invention is to provide a sterilizing apparatus which sprays out an antiseptic solution at a substantially small velocity; the spray angle of the solution is sufficiently large; the zone covered by the sprayed solution is laterally extended; the consumption of the solution is minimized; the apparatus requires less frequent maintenance; and the apparatus can be operated quietly.

In order to achieve the above object, the sterilizing apparatus according to the present invention comprises an atomizing device of the antiseptic solution which is disposed at the top part of a sterilizing room. The atomizing device has a vibrator transducer which is vibrated at an ultrasonic frequency and a downwardly extending multi-step columnar horn which is fixedly attached to the vibrator transducer. The horn magnifies the amplitude of the ultrasonic vibration transmitted from the vibrator transducer to the maximum amplitude at the bottom end of the horn. An antiseptic solution supply device supplies an antiseptic solution to the bottom end of the vibrating horn, so that the supplied solution is atomized by the ultrasonic vibration and forms a mist of the antiseptic solution in a sterilizing room. Then, the object is sterilized by the mist of the antiseptic solution in the sterilizing room.

More specifically, the antiseptic solution supply device includes a generally cylindrically shaped antiseptic solution holding receptacle which is disposed coaxially with the horn about the center axis of the horn. The holding receptacle has solution outlet grooves in a bottom wall thereof contiguous with the surface of the bottom section of the horn so that the antiseptic solution supplied into the holding receptacle exits through the grooves and attaches to the surface of the bottom section of the horn, thereby being atomized because of the ultrasonic vibration of the horn. The bottom end of the horn is tapered towards the center axis of the horn so that the atomized solution spreads about the bottom end of the horn in a mist state. The bottom wall of the solution holding receptacle has downwardly projecting flow directors contiguous with the solution outlet grooves, so that the flow directors properly guide the solution exiting through the outlet grooves. Because the outlet grooves are disposed on both the left and right sides of the horn, as viewed by the user, the atomized solution is spread more in the lateral direction than the longitudinal direction, as viewed by the user.

The apparatus is equipped with an automatic detector which detects the object of the sterilization, and a control unit which causes the vibrator transducer and the antiseptic solution supply device to be activated automatically as soon as the detector has detected the object placed in the sterilizing room.

BRIEF DESCRIPTION OF THE DRAWINGS

FIG. 12 shows an essential part of the sterilizing apparatus of the third embodiment.

FIG. 13 is a timing chart showing exact timings of activations and deactivations of the photo sensor (FIG. 13a), the vibrator transducer and the oscillator (FIG. 13b) and the magnetic pump (FIG. 13c) employed in the sterilizing apparatus.

DETAILED DESCRIPTION OF THE PREFERRED EMBODIMENTS

Figure 1:
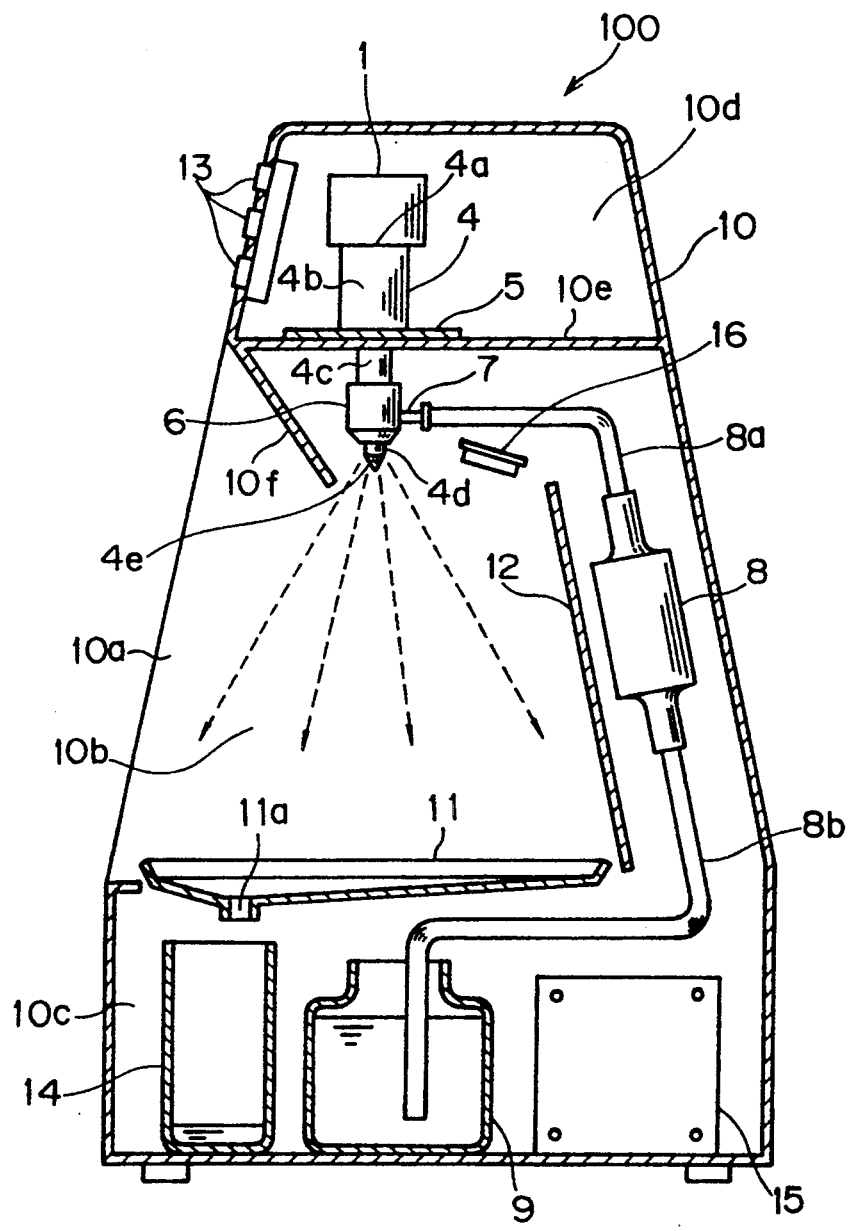
FIG. 1 is a side elevational sectional view showing an embodiment of the sterilizing apparatus according to the present invention.

Referring to FIGS. 1 to 6, numeral 100 denotes a sterilizing apparatus of an embodiment according to the present invention. Numeral 1 denotes a vibrator transducer which is driven by the electrical output of an oscillator 2 at an ultrasonic frequency of 30 kHz to 80 kHz and generates an ultrasonic vibration. The output frequency of the oscillator 2 is controllable. In this embodiment, the vibrator transducer 1 has a resonance frequency of approximately 60 kHz and, accordingly, the output frequency of the oscillator 2 is set for approximately 60 kHz and the vibration transducer 1 outputs an ultrasonic vibration of approximately 60 kHz. A Langevin-type vibrator transducer, for example, may be used for the vibrator transducer 1. The oscillator 2 is driven by a power supply 3 which works on a normal commercial AC power.

Numeral 4 denotes a multi-step columnar horn which is disposed generally vertically. The vibrator transducer 1 is fixedly attached to the horn on the top surface 4a of the horn 4. The horn 4 magnifies the amplitude of the ultrasonic vibration generated by the vibrator transducer 1 and is transmitted to the horn 4 through the top surface 4a. The horn 4, in this embodiment, is designed to have the same resonance frequency as of the vibrator transducer 1. The horn 4 is integrally made of aluminum and it consists of four sections. They are, from the top end, an upper section 4b, a mid section 4c, a lower section 4d, and a vibration output tip 4e. Each of the three sections 4b, 4c, 4d has a columnar form and the diameters of the sections 4c and 4d are smaller than the diameters of sections 4b and 4c, respectively. In other words, the diameters of the horn 4 become smaller in steps from the top towards the bottom. In this embodiment, the diameters of the mid section 4c and the lower section 4d are 15.0 mm and 7.9 mm, respectively, and the vertical length of the lower section 4d is 20.0 mm. At the very bottom end under the lower section 4d is the output tip 4e, which, in this embodiment, is of conical form. The horn 4 is supported by a horn supporting member 5 at the bottom end of the upper section 4b and the horn supporting member 5 is fixed to a housing 10 as mentioned later in detail.

The amplitude of the ultrasonic vibration is magnified as the vibration is transmitted from the top surface 4a to the output tip 4e and the amplitude becomes maximum at the output tip 4e because of the decreasing diameters of the horn 4. The amplitude of the vibration in the vertical direction at the horn tip 4e, in this embodiment, is 20 to 40 μm. The tip angle, shown as "θ" in FIG. 3, of the conical output tip 4e is determined according to the desired spreading angle of the antiseptic solution. The proper tip angle for hand or finger sterilization, for example, is 60° to 135°.

Figure 3:
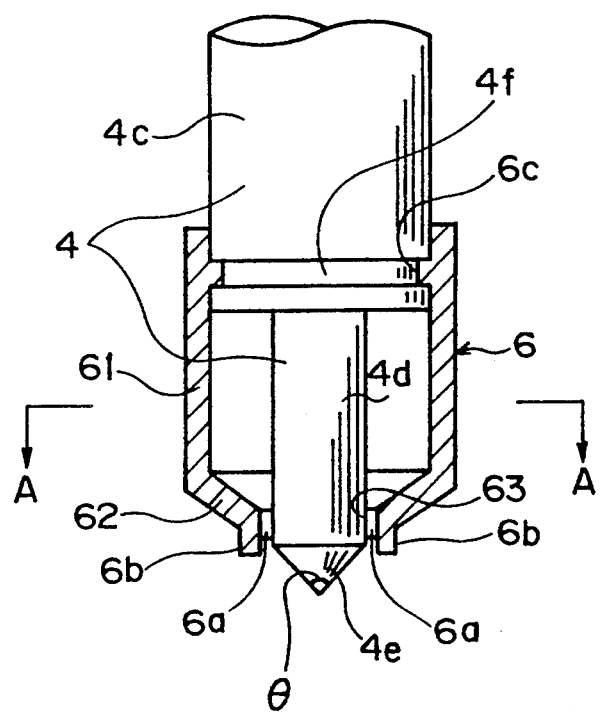
FIG. 3 is a partial elevational view showing a lower part of a horn and an antiseptic solution holding receptacle, in section, employed in the first embodiment of the sterilizing apparatus, as viewed from the front of the apparatus.
Figure 4:
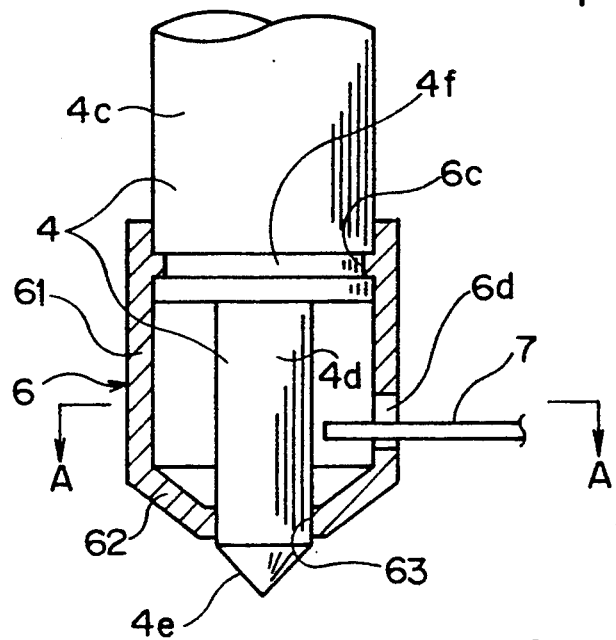
FIG. 4 is a partial elevational view showing a lower part of the horn and the antiseptic solution holding receptacle, in section, and an antiseptic solution supply pipe employed in the sterilizing apparatus, as viewed from a side of the apparatus.

Numeral 6 denotes an antiseptic solution holding receptacle, made of a synthetic resin, for temporarily holding the antiseptic solution. The holding receptacle 6 has a generally cylindrically-shaped side wall 61 in the upper part thereof, a bottom wall 62, and a circular bottom hole 63 that is surrounded by the bottom wall 62. The holding receptacle 6 is disposed coaxially with the horn 4 with respect to the longitudinal center axis of the horn 4 so as to generally surround the lower section 4d of the horn 4, as best shown in FIGS. 3 and 4. The bottom wall 62 is downwardly sloped to the surface of the lower section 4d of the horn 4. The horn 4 extends from inside the holding receptacle 6 downwardly through the bottom hole 63, so that the vibration output tip 4e of the horn 4 is located outside the holding receptacle 6 and below the bottom wall 62.

Figure 5:
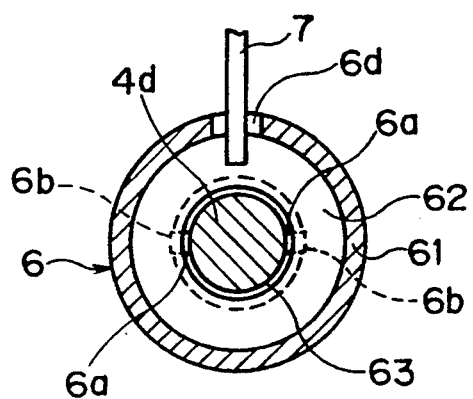
FIG. 5 is the horizontal sectional view, taken along line A—A shown in FIG. 3 and/or FIG. 4.
Figure 6:
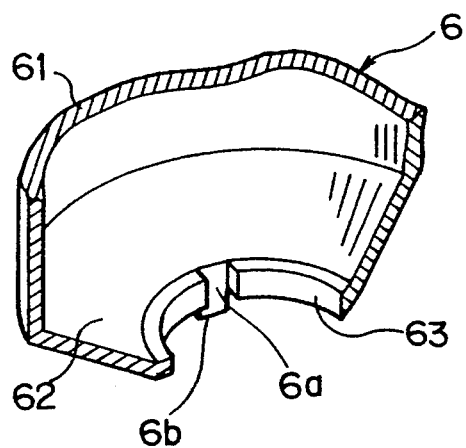
FIG. 6 is a perspective cutaway view showing a bottom portion of the antiseptic solution holding receptacle.
Figure 7:
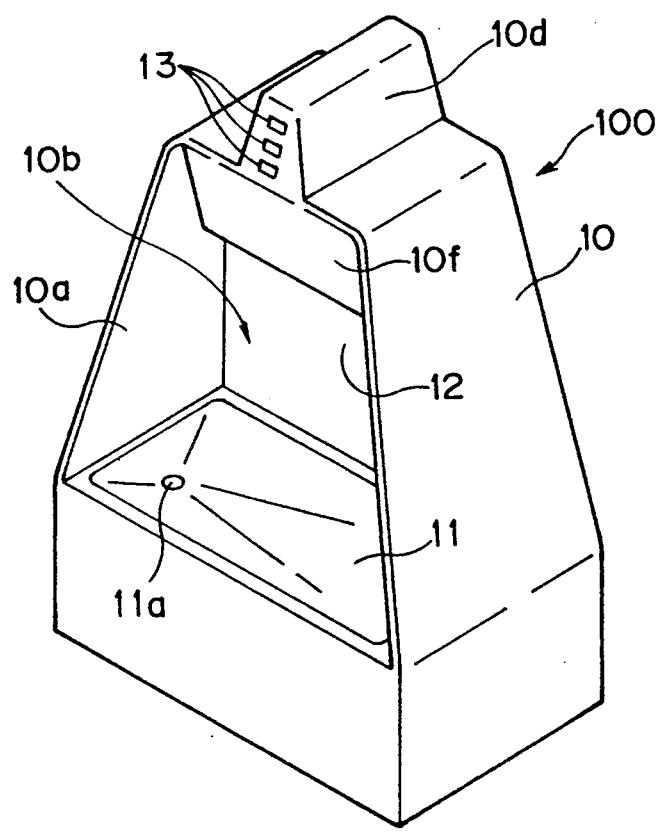
FIG. 7 is a perspective view of the sterilizing apparatus shown in FIG. 1.

The holding receptacle 6 also has a pair of rectangular-formed solution outlet holes 6a in the bottom wall 62 and on the periphery of the bottom hole 63. The dimensions of the outlet holes 6a, in this embodiment, are 2.0 mm (width), 1.0 mm (depth) and 0.5 mm (height). The outlet holes 6a are disposed contiguous with the surface of the lower section 4d of the horn 4, at the opposing sides of the lower section 4d with respect to the vertical center axis of the horn 4, and in the proximity of the output tip 4e, as shown in FIGS. 3 and 5. Except for the outlet holes 6a, the bottom wall 62 of the holding receptacle 6 tightly contacts with the surface of the lower section 4d of the horn 4. The holding receptacle 6 further has a downwardly projecting flow director 6b at the position contiguous with each of the outlet holes 6a, as best shown in FIGS. 3 and 6, so that each of the flow directors 6b opposes the surface of the lower section 4d of the horn 4 and each of the outlet holes 6a is disposed between the surface of the lower section 4d of the horn 4 and the flow director 6b. The width and the height of the flow directors 6b, in this embodiment, are 2.0 mm and 2.0 mm, respectively, and the tops of the flow directors 6b are even with the tops of the outlet holes 6a.

The mid section 4c of the horn 4 has a peripheral circular groove 4f in the proximity of the lower end thereof and the holding receptacle 6 has on its inside a circular projection 6c in the proximity of the top end thereof, as shown in FIGS. 3 and 4. The circular projection 6c engages with the circular groove 4f so that the holding receptacle 6 is firmly held by the mid section 4c of the horn 4. The position of the circular groove 4f and the circular projection 6c corresponds to the position of a node of the waves of the ultrasonic vibration in the horn 4. The holding receptacle 6 has a side hole 6d (FIGS. 4, 5) so that any excessive antiseptic solution can escape therethrough and the solution can smoothly exit through the outlet holes 6a. An antiseptic solution supply pipe 7 extends through the side hole 6d into the holding receptacle 6.

Referring to FIG. 1, numeral 8 denotes a magnetic pump, numerals 8a and 8b denote flexible tubes, and numeral 9 denotes a supply tank for the antiseptic solution. The pump 8 feeds the antiseptic solution into the holding receptacle 6 from the supply tank 9 through the tubes 8a, 8b and the pipe 7.

Now, the overall structure of the sterilizing apparatus 100 will be explained in reference to FIG. 1.

Numeral 10 denotes a housing, which is the basic frame of the apparatus and is configured downwardly larger in both width and depth. The housing 10 has a front opening 10a and a sterilizing room 10b so that the user extends his hands or other object to be sterilized through the opening 10a into the sterilizing room 10b. The bottom section in the housing 10 is a bottom gadget room 10c. Between the sterilizing room 10b and the bottom gadget room 10c is disposed a sink 11 having a drain hole 11a. On the back side of the sterilizing room 10b is disposed a separation wall 12 so as to form a space between the separation wall 12 and the rear wall of the housing 10. The top section in the housing 10 is a top gadget room 10d. Between the sterilizing room 10b and the top gadget room 10d is disposed a horizontal separation member 10e which is fixedly connected to the housing 10. The horn supporting member 5 is mounted on the separation member 10e. As mentioned above, the horn 4 is supported by a horn supporting member 5 at the bottom end of the upper section 4b of the horn 4, and the position of the circular groove 4f (FIGS. 3, 4) and the circular projection 6c corresponds to the position of a node of the ultrasonic vibration waves in the horn 4. Therefore, any escape of the vibration energy of the horn 4 to the housing 10 through the horn supporting member 5 and the separation member 10e is minimized. The vibrator transducer 1 and the upper section 4b of the horn 4 are disposed in the top gadget room 10d and the mid section 4c, the lower section 4d, and the output tip 4e of the horn 4 are disposed in the upper area of the sterilizing room 10b. On the front side (i.e. left-hand side, as viewed in FIG. 1) of the top gadget room 10d is disposed an operation displays 13 including light emitting diodes. An inclined shield panel 10f downwardly and inwardly extends from the top of the front opening 10a so that the panel 10f shields the front side of the horn 4. In the bottom gadget room 10c, a waste solution receptacle 14, under the drain hole 11a, the supply tank 9 and a control device 15 are disposed from the front to the rear in the respective order.

Still referring to FIG. 1, numeral 16 denotes a photo sensor disposed in the upper part in the sterilizing room 10b. The photo sensor 16 has light emitting and light receiving elements so as to receive a reflected light from the object to be sterilized placed in the sterilizing room 10b, thereby recognizing the presence of the object.

Figure 2:
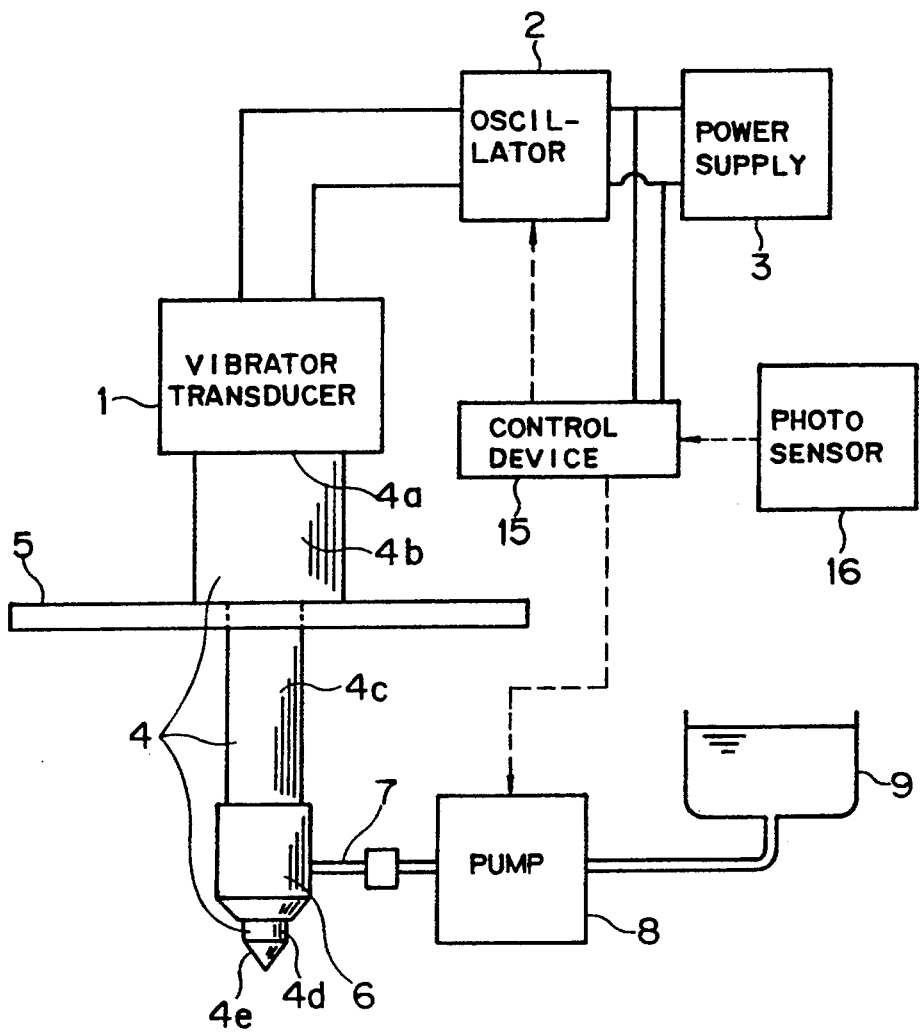
FIG. 2 is an operational block diagram of the sterilizing apparatus shown in FIG. 1.

Referring to FIGS. 1 and 2, the control device 15 is electrically connected with the oscillator 2 for the vibrator transducer 1, the magnetic pump 8 and the photo sensor 16 so that when the photo sensor 16 recognizes the presence of the object to be sterilized the control device 15 causes all of the oscillator 2, the vibrator transducer 1 and the pump 8 to be activated for a predetermined time period.

Now, the function of the sterilizing apparatus 100 will be explained in reference to FIGS. 1 to 10.

First, the user extends his/her hands or other object to be sterilized into the sterilizing room 10b. As soon as the presence of the object is recognized by the photo sensor 16, the control device 15 causes the oscillator 2 and the pump 8 to be activated. Then the oscillator 2 transmits an electrical power of the predetermined ultrasonic frequency to the vibrator transducer 1 and, almost simultaneously, the pump 8 feeds the antiseptic solution from the supply tank 9 into the solution holding receptacle 6 at a predetermined flow rate. Thus the vibrator transducer 1 transmits an ultrasonic vibration, of, in this embodiment, approximately 60 kHz, to the horn 4 through the top surface 4a of the horn 4. The amplitude of the vibration is magnified in the horn 4 as the vibration travels in the horn 4 downwardly because of the decreasing diameters of the horn 4 towards the output tip 4e of the horn 4. The ultrasonic vibration of the magnified amplitude is, therefore, outputted from the output tip 4e of the horn 4. At this time, the nodes and the loops of the vibration waves are alternately present along the longitudinal axis of the horn 4 and the most magnified loop is present at the output tip 4e so that the tip 4e is vibrated at the maximum amplitude as mentioned above.

Figure 8:
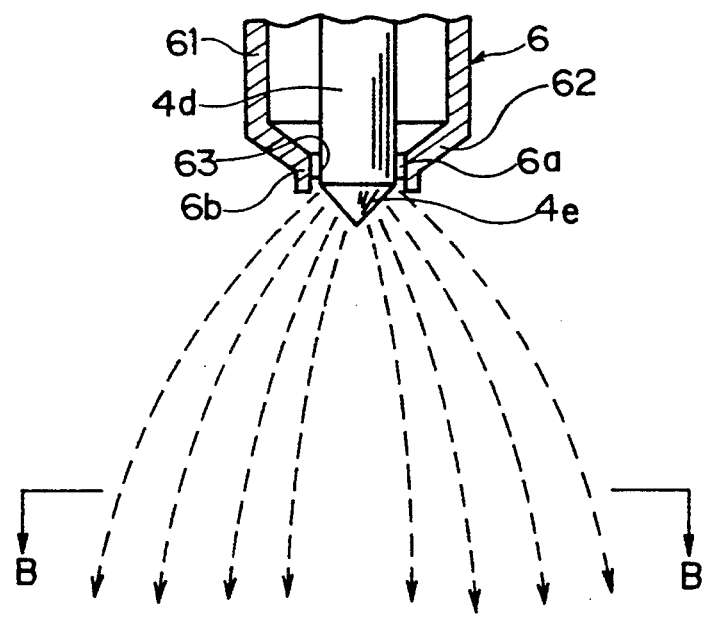
FIG. 8 elevationally shows a bottom end portion of the horn, a lower portion of the antiseptic solution holding receptacle, in section, and a diagrammatic view of the atomized antiseptic solution being sprayed.
Figure 9:
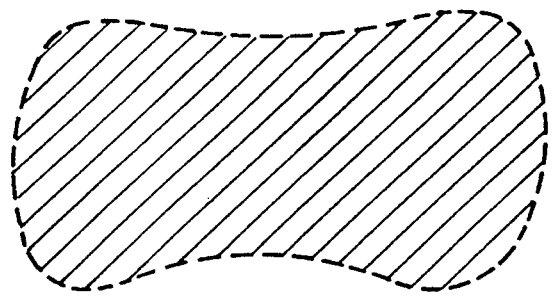
FIG. 9 is a diagrammatic view showing the horizontal section, as taken along line B—B shown in FIG. 8, of the spreading zone of the atomized antiseptic solution of the first embodiment.

On the other hand, the antiseptic solution is supplied into the holding receptacle 6 from the pipe 7. The solution temporarily stays in the holding receptacle 6, then, gradually flows out through the outlet holes 6a. The solution exiting from the holding receptacle 6 through the holes 6a then reaches the surface of the output tip 4e which is in vibration. As soon as the solution reaches the output tip 4e, the solution on the output tip 4e is subjected to the ultrasonic vibration of the maximum amplitude. Then, by the well known principle in the art, the ultrasonic vibration of the output tip 4e causes the solution on the output tip 4e to be broken apart into numerous extremely fine droplets, i.e. the solution in a state of mist. This effect can also be referred to as atomization of the solution, and the solution in the state of mist may therefore be also called "atomized solution". The solution exiting through the outlet holes 6a is guided to the areas between the downwardly projecting flow directors 6b of the holding receptacle 6 and the surface of the lower section 4d of the horn 4 by capillary action. This capillary action causes to maintain a smooth and continuous outflow of the solution from the holding receptacle 6. Since the two outlet holes 6b and the respective two flow directors 6b are disposed on the opposing sides of the horn 4, with respect to the vertical center axis of the horn 4, the solution having exited through the outlet holes 6a flows also to the two corresponding opposing areas on the surface of the tip 4e of the horn 4. Therefore, the atomized antiseptic solution spreads mainly to the same two opposing directions corresponding to the positions of the opposing outlet holes 6a. On the other hand, the outlet holes 6a are disposed at the 3 o'clock and the 9 o'clock positions assuming that the user position (in front) is the 6 o'clock position, as shown in FIG. 5. Thus, the spreading direction of the mist of the solution has the laterally extended orientation, with respect to the position of the user, as shown in FIGS. 8 and 9.

Figure 10:
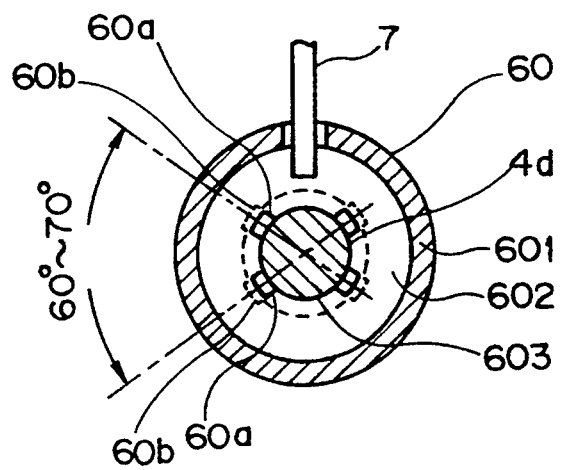
FIG. 10 is a horizontal sectional view similar to FIG. 5, but showing an antiseptic solution holding receptacle of the second embodiment.

FIG. 10 shows a horizontal section of an alternative antiseptic solution holding receptacle 60 of the second embodiment of the sterilizing apparatus 100 according to the present invention. This alternative holding receptacle 60 has a generally cylindrically-shaped side wall 601, a bottom wall 602, a bottom hole 603, two opposing pairs of solution outlet holes 60a in the bottom wall 602, and corresponding two opposing pairs of downwardly projecting flow directors 60b contiguous with the respective outlet holes 60a. As shown in FIG. 10, a pair of imaginary lines, each passing the opposing pair of the holes 60a or the flow directors 60b, intersect each other at an angle of 60° to 70°. Except for the numbers and the positioning of the outlet holes 60a and the flow directors 60b, the basic construction and the arrangement of the alternative holding receptacle 60 are the same as those of the holding receptacle 6 of the first embodiment.

Figure 11:
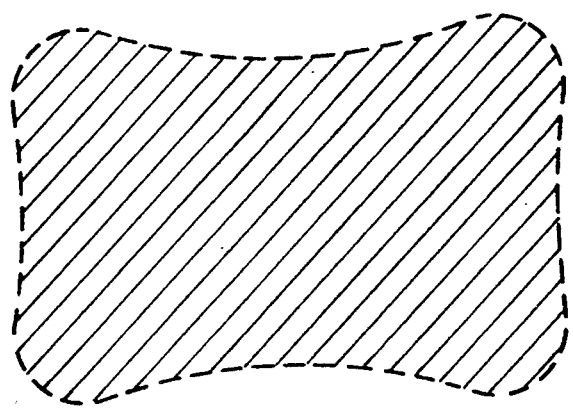
FIG. 11 is a diagrammatic view similar to FIG. 9, but showing a horizontal section of the spreading zone of the atomized antiseptic solution when the antiseptic solution holding receptacle of the second embodiment shown in FIG. 10 is used.

FIG. 11 diagrammatically shows a horizontal section of the spreading zone of the atomized antiseptic solution when the alternative holding receptacle 60 of the second embodiment is used. It will be noted that the spreading zone of the second embodiment as shown in FIG. 11 is more extended in the longitudinal direction, with respect to the position of the user, as compared with the spreading zone of the first embodiment as shown in FIG. 9.

FIG. 12 shows an essential part of the sterilizing apparatus of the third embodiment according to the present invention. In this embodiment, an alternative horn 40 and an alternative antiseptic solution holding receptacle 600 are different from the horn 4 and the holding receptacle 6, respectively. The holding receptacle 600 is designed to accept the pipe 7 so that the pipe 7 is directed precisely toward the center of the horn 40, whereby the antiseptic solution is evenly distributed around the horn 40. The holding receptacle 600 additionally has a ventilating hole 600e above a side hole 600d so that the antiseptic solution may smoothly flows out of the outlet holes. The horn 40 has a mounting groove 40f similar to the groove 4f and is mounted on a horn supporting member 50 that engages with the mounting groove 40f. The horn supporting member 50 and the holding receptacle 600 are fixed to the separation member 10e by screws 50a.

FIG. 13 is a timing chart showing exact timings of activations and deactivations of the photo sensor 16 (FIG. 13a), the vibrator transducer 1 and the oscillator 2 (FIG. 13b) and the magnetic pump 8 (FIG. 13c). T1 (approx. 0.2 sec) is a delay time after the oscillator 2 and the vibrator transducer 1 are turned on until the magnetic pump 8 is turned on. This time delay is intended for smooth initiation of resonation of the horn 4 or 40, because if the load (the solution) is applied to the horn 4 or 40 before the horn 4 or 40 is properly resonated, the initiation of the resonation may be prevented by the load. T2 (approx. 1.0 sec) is a delay time after the magnetic pump 8 is turned off until the oscillator 2 and the vibrator transducer 1 are turned off. This delay time is intended for keeping the horn 4 or 40 vibrating for an extra second in order to atomize the residual solution in the holding receptacle 6 and empty the holding receptacle 6 completely at each completion of the sterilizing operation.

As mentioned above, the dimensions of the outlet holes 6a, i.e. 2.0 (w)×1.0 (d)×0.5 (h) mm, are substantially large, as compared to the small diameter, normally 0.2–0.3 mm, of a nozzle of a conventional jet-type sterilizing apparatus. This makes the sterilizing apparatus 100 of the present invention virtually free of clogging problem. In addition, since the sterilizing apparatus 100 employs an atomizing device for the antiseptic solution utilizing an ultrasonic vibration instead of a jetting from a nozzle, the apparatus creates no undesirable jetting noise. Furthermore, the atomized solution falls in the sterilizing room 10b much more slowly than jetted solution, without splash, the solution would not reach the clothes or any other unintended parts of the user, and the solution would not be wasted. The tip 4e or 40e of the horn 4 or 40 enables the spreading angle of the atomized solution to be sufficiently large, so that the vertical distance between the horn 4 or 40 and the object to be sterilized can be minimized and, therefore, the overall size of the apparatus may be made compact. Since the mist of the antiseptic solution is spread mainly towards the two lateral and opposite directions from each other with respect to the position of the user, all of the fingers or both hands of the user can evenly be sterilized. Since the photo sensor 16 in the sterilizing room 10b and the control device 15 enable the automatic activation of the apparatus, the sterilization is easily and conveniently performed.

As additional alternative embodiments, the solution holding receptacle 6, 60 or 600 may be replaced by other proper solution feeding device and the photo sensor 16 may be replaced by other type of switching device such as a foot-pedal switch. The output tip 4e or 40e may be formed in either a semispherical form, a partial spherical form or a paraboloidal form, instead of the conical form of the above mentioned embodiments.

It will be understood that various changes and modifications may be made in the above described embodiments which provide the characteristics of this invention without departing from the spirit and principle thereof particularly as defined in the following claims.

What is claimed is:

1. A sterilizing apparatus comprising:
   (a) a frame;
   (b) a downwardly extending vibrator horn supported by said frame, said vibrator horn having a vibration output tip at a low end thereof, said output tip being downwardly tapered;
   (c) a vibrator transducer connected to said vibrator horn so as to vibrate said vibrator horn at an ultrasonic frequency;
   (d) an oscillator for generating an electrical power of the ultrasonic frequency and energizing said vibrator transducer therewith;
   (e) a power supply for energizing said oscillator;
   (f) an antiseptic solution holding receptacle, having a side wall and bottom wall extending substantially transverse to said side wall and a bottom hole extending through said bottom wall, for temporarily holding antiseptic solution therein, said holding receptacle being disposed in a manner that a part of said horn is disposed inside said holding receptacle, said horn extends from inside said holding receptacle downwardly through said bottom hole and said vibration output tip of said horn is disposed below said bottom wall, said holding receptacle having at least one solution outlet groove extending through and opening to said bottom groove said bottom wall, said solution outlet groove being adjacent to a surface of said horn; and
   (g) means for supplying an antiseptic solution into said holding receptacle, so that the antiseptic solution supplied into said holding receptacle gradually exits from said holding receptacle through said solution outlet groove and the antiseptic solution having exited from said holding receptacle comes into contact with said output tip of said horn, whereby an ultrasonic vibration of said output tip causes the antiseptic solution to be atomized.

2. A sterilizing apparatus according to claim 1, wherein said antiseptic solution holding receptacle additionally has a flow director projecting downwardly from said bottom wall for maintaining a smooth and continuous outflow of the solution from said holding receptacle, said flow director being disposed contiguous with said solution outlet groove opposing the surface of said horn so that said solution outlet groove is interposed between the surface of said horn and said flow director.

3. A sterilizing apparatus comprising:

(a) a frame;

(b) a downwardly extending vibrator horn supported by said frame, said vibrator horn having a vibration output tip at a low end thereof, said output tip being tapered;

(c) a vibrator transducer connected to said vibrator horn so as to vibrate said vibrator horn at an ultrasonic frequency;

(d) an oscillator for generating an electrical power of the ultrasonic frequency and energizing said vibrator transducer therewith;

(e) a power supply for energizing said oscillator;

(f) an antiseptic solution holding receptacle, having a sidewall and a bottom wall extending substantially transverse to each side wall and a bottom hole extending through said bottom wall, for temporarily holding antiseptic solution therein, said holding receptacle being disposed in a manner that a part of said horn is disposed inside said holding receptacle, said horn extends from inside said holding receptacle downwardly through said bottom hole and said vibration output tip of said horn is disposed below said bottom wall, said holding receptacle having a first solution outlet groove and a second solution outlet groove extending through said bottom wall and opening to said bottom hole, said first outlet groove and said second outlet groove being adjacent to a surface of said horn in an opposing relationship with each other with respect to a center axis of said horn; and (g) means for supplying an antiseptic solution into said holding receptacle, so that the antiseptic solution supplied into said holding receptacle gradually exits from said holding receptacle through said first and second solution outlet grooves and the antiseptic solution having exited from said holding receptacle comes into contact with said output tip of said horn, whereby an ultrasonic vibration of said output tip causes the antiseptic solution to be atomized.

4. A sterilizing apparatus according to claim 3, wherein said antiseptic solution holding receptacle additionally has a first flow director and a second flow director for maintaining a smooth and continuous outflow of the solution from said holding receptacle, said first flow director and said second flow director projecting downwardly from said bottom wall and being disposed contiguous with said first solution outlet groove and said second solution outlet groove, respectively, opposing the surface of said horn so that said first outlet groove and said second outlet groove are interposed between the surface of said horn and said first flow director and said second flow director, respectively.

5. A sterilizing apparatus comprising:

(a) a frame;

(b) a downwardly extending vibrator horn supported by said frame, said vibrator horn having a vibration output tip at a low end thereof, said output tip being downwardly tapered;

(c) a vibrator transducer connected to said vibrator horn so as to vibrate said vibrator horn at an ultrasonic frequency;

(d) an oscillator for generating an electrical power of the ultrasonic frequency and energizing said vibrator transducer therewith;

(e) a power supply for energizing said oscillator;

(f) an antiseptic solution holding receptacle, having a side wall and a bottom wall extending substantially transverse to said side wall and a bottom hole extending through said bottom wall, for temporarily holding antiseptic solution therein, said holding receptacle being disposed in a manner that a part of said horn is disposed in said holding receptacle, said horn extends from inside said holding receptacle downwardly through said bottom hole and said vibration output tip of said horn is disposed below said bottom wall, said holding receptacle having a first solution outlet groove, a second solution outlet groove, a third solution outlet groove and a fourth solution outlet groove, all extending through said bottom wall and opening to said bottom hole, all of said four solution outlet grooves being adjacent to a surface of said horn and being arranged in a manner that a first imaginary line passing said first and second solution outlet grooves and a second imaginary line passing said third and fourth solution outlet grooves intersect each other at a center axis of said horn at an angle within a range from 60° to 70°; and (g) means for supplying an antiseptic solution into said holding receptacle, so that the antiseptic solution supplied into said holding receptacle gradually exits from said holding receptacle through said four solution outlet grooves and the antiseptic solution having exited said holding receptacle comes into contact with said output tip of said horn, whereby an ultrasonic vibration of said output tip causes the antiseptic solution to be atomized.

6. A sterilizing apparatus according to claim 5, wherein said antiseptic solution holding receptacle additionally has a first flow director, a second flow director, a third flow director and a fourth flow director for maintaining a smooth and continuous outflow of the solution from said holding receptacle, said first, second, third and fourth flow directors projecting downwardly from said bottom wall and being disposed contiguous with said first, second, third and forth solution outlet grooves, respectively, opposing the surface of said horn so that said first, second, third and fourth outlet grooves are interposed between the surface of said horn and said first, second, third and fourth flow directors, respectively.

* * * * *